United States Patent
Xie et al.

(10) Patent No.: US 8,580,702 B2
(45) Date of Patent: Nov. 12, 2013

(54) TOLUENE SELECTIVE DISPROPORTIONATION CATALYST

(75) Inventors: Zaiku Xie, Shanghai (CN); Dejin Kong, Shanghai (CN); Zhirong Zhu, Shanghai (CN); Wei Li, Shanghai (CN); Qingling Chen, Shanghai (CN); Rong Zhang, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 408 days.

(21) Appl. No.: 12/513,261

(22) PCT Filed: Nov. 2, 2007

(86) PCT No.: PCT/CN2007/003120
§ 371 (c)(1),
(2), (4) Date: Jun. 16, 2009

(87) PCT Pub. No.: WO2008/052445
PCT Pub. Date: May 8, 2008

(65) Prior Publication Data
US 2010/0048382 A1    Feb. 25, 2010

(30) Foreign Application Priority Data
Nov. 2, 2006  (CN) .......................... 2006 1 0117849

(51) Int. Cl.
*B01J 29/06* (2006.01)
*C07C 5/22* (2006.01)

(52) U.S. Cl.
USPC ............. 502/64; 502/63; 502/65; 502/69; 502/71; 585/470; 585/475

(58) Field of Classification Search
USPC ............ 502/63, 64, 65, 66, 69, 71; 585/470, 585/475
See application file for complete search history.

(56) References Cited

U.S. PATENT DOCUMENTS

| | | | |
|---|---|---|---|
| 4,472,518 A | | 9/1984 | Chu |
| 4,477,583 A | * | 10/1984 | Rodewald ...................... 502/71 |
| 5,243,117 A | * | 9/1993 | Chang et al. .................. 585/467 |
| 5,552,357 A | * | 9/1996 | Lago et al. ..................... 502/63 |
| 6,486,373 B1 | * | 11/2002 | Abichandani et al. ........ 585/475 |
| 2001/0002383 A1 | | 5/2001 | Hidaka et al. |
| 2006/0011514 A1 | * | 1/2006 | van den Berge et al. 208/120.01 |
| 2006/0173225 A1 | * | 8/2006 | Das et al. ...................... 585/467 |
| 2008/0118431 A1 | * | 5/2008 | Vermeiren et al. ............ 423/713 |

FOREIGN PATENT DOCUMENTS

| | | |
|---|---|---|
| CN | 00119772 | 3/2002 |
| CN | 1340485 A | 3/2002 |
| CN | 1340487 A | 3/2002 |
| CN | 1340488 A | 3/2002 |

* cited by examiner

*Primary Examiner* — Elizabeth Wood
(74) *Attorney, Agent, or Firm* — Scully, Scott, Murphy & Presser, P.C.

(57) ABSTRACT

The present invention discloses a catalyst for toluene shape selective disproportionation, comprising: a) 45 to 95 wt % of ZSM-5 molecular sieve having an average particle size of from 0.3 to 6 μm and a molar ratio of $SiO_2$ to $Al_2O_3$ of from 20 to 120; b) 0.01 to 30 wt % of at least one metal selected from the group consisting of Group IIB metals, Group IIIB metals, rare earth elements and Group VIII metals other than nickel, or oxide(s) thereof; c) 0 to 20 wt % of at least one metal selected from the group consisting of Group VA metals, Group VIB metals and alkaline earth metals, or oxide(s) thereof; d) 1 to 25 wt % of a silica inert surface coating derived from an organopolysiloxane; and e) 1 to 50 wt % of a binder. The present invention further discloses a process for shape selectively disproportionating toluene into p-xylene, comprising contacting a reaction stream containing toluene with the catalyst for toluene shape selective disproportionation under toluene disproportionation conditions.

23 Claims, No Drawings

TOLUENE SELECTIVE DISPROPORTIONATION CATALYST

CROSS REFERENCE OF RELATED APPLICATIONS

The present application claims the benefit of the Chinese Patent Application No. 200610117849.2, filed on Nov. 2, 2006, which is incorporated herein by reference in its entirety and for all purposes.

FIELD OF THE INVENTION

The present invention relates to a catalyst for toluene shape selective disproportionation, preparation thereof and use thereof.

BACKGROUND OF THE INVENTION

Disproportionation of toluene can convert toluene into more valuable benzene and xylenes. The xylene products are generally mixtures of three isomers in thermodynamical equilibrium, and the most valuable p-xylene accounts for only about 24%. Therefore, shape selective disproportionation as a new process is proposed to selectively produce p-xylene. Conventional catalysts for the toluene disproportionation contain mordenite having a larger channel diameter as the main active component and therefore exhibit no shape selectivity to the three isomers of xylenes. ZSM-5 molecular sieve has a three dimensional channel system consisting of 10-member rings. It has been found that the channels of ZSM-5 molecular sieve permit quick diffusion of p-xylene having a molecular diameter of 0.63 nm, while o-xylene and m-xylene having a molecular diameter of 0.69 nm have much less diffusion coefficient. The diffusion coefficients of the species present in toluene disproportionation system in the channels of ZSM-5 molecular sieve have the following relationship: benzene≥toluene>ethylbenzene≅p-xylene>o-xylene≅m-xylene. This implies there is a possibility that toluene disproportionation may be shape selectively catalyzed to obtain a concentration of p-xylene isomer in the xylene product much higher than the thermodynamical equilibrium concentration of p-xylene. However, since the p-xylene-rich product diffused out from the molecular sieve channels will undergo isomerization reaction on acid sites existing on external surfaces of the molecular sieve, and the rate of the isomerization reaction is much higher than the rate of the disproportionation reaction, the product will quickly reach thermodynamical equilibrium composition. Although some investigations show that a shape selectivity can be achieved by using ZSM-5 having a large grain size at a higher space velocity and a lower conversion, such a process is not practical in industry.

U.S. Pat. Nos. 5,367,099, 5,607,888 and 5,476,823 disclose the modification of ZSM-5 molecular sieve structure, i.e., reducing the size of pore opens and shielding acid sites on external surfaces, to prepare a catalyst for selective toluene disproportionation. In the preparation of the catalyst, a thermally decomposable polymer is deposited on the external surfaces of the molecular sieve, and then the molecular sieve is subjected to a high temperature treatment to thermally decompose the polymer to form an inert coating, which will shield the acid sites on the external surfaces of the molecular sieve and also reduce the size of the pore opens to an extent. Such a surface modification enhances greatly the p-xylene selectivity of the catalyst.

U.S. Pat. No. 5,365,003 discloses a process and a catalyst for a shape selective hydrocarbon conversion. The catalyst is prepared by a process comprising: agglomerating a mixture comprising molecular sieve crystals, organosilicon compound and optionally a binder material; and calcining the resulting agglomerate. The catalyst may be subsequently contacted with a mixture of a high-efficiency p-xylene trim selectivating agent and substituted aromatic at reaction conditions for converting toluene to xylene to produce a twice selectivated catalyst, wherein the high-efficiency p-xylene trim selectivating agent includes, for example, organosilicon compounds.

Chinese Patent Application No. 00119772.X discloses a noble metal-modified catalyst for toluene selective disproponionation, comprising 20 to 90 wt % of ZSM-5 molecular sieve in hydrogen form, 0.005 to 5 wt % of at least one noble metal selected from ruthenium, rhodium, palladium, rhenium, platinum and gold, and 9 to 75 wt % of silica or alumina as a binder. The catalyst further comprises optionally at least one element selected from chromium, nickel, molybdenum, tungsten, antimony and bismuth. Although the catalyst containing noble metal-modified ZSM-5 molecular sieve in hydrogen form may enhance catalytic activity for toluene selective disproportionation, the noble metal-modified molecular sieve catalyst will cause relatively significant toluene hydrogenation and dealkylation side-reactions, thereby reducing the yield of the p-xylene product.

Although some investigations have been conducted in the shape selective catalysis of toluene disproportionation, there still need catalysts for toluene shape selective disproportionation, which have higher catalytic activities and, at the same time, will cause little or no toluene hydrogenation and dealkylation side-reactions.

SUMMARY OF THE INVENTION

The inventors have made diligently investigations, and consequently found that a metal-modified ZSM-5 molecular sieve catalyst can be provided by selecting suitable modifying element(s) or oxides thereof and controlling their amounts, in combination with the use of a silica inert surface coating, which catalyst has higher catalytic activity for toluene shape selective disproportionation and high p-xylene selectivity and will not cause remarkable side-reactions of toluene hydrogenation and dealkylation. So the invention has been made.

An object of the invention is to provide a catalyst for toluene shape selective disproportionation, comprising:

a) 45 to 95 wt % of ZSM-5 molecular sieve having an average particle size of from 0.3 to 6 μm and a molar ratio of $SiO_2$ to $Al_2O_3$ of from 20 to 120;

b) 0.01 to 30 wt % of at least one metal selected from the group consisting of Group IIB metals, Group IIIB metals, rare earth elements and Group VIII metals other than nickel, or oxide(s) thereof;

c) 0 to 20 wt % of at least one metal selected from the group consisting of Group VA metals, Group VIB metals and alkaline earth metals, or oxide(s) thereof;

d) 1 to 25 wt % of a silica inert surface coating derived from an organopolysiloxane; and e) 1 to 50 wt % of a binder.

Another object of the invention is to provide a process for shape selectively disproportionating toluene into p-xylene, comprising contacting a reaction stream containing toluene with the catalyst for toluene shape selective disproportionation according to the invention under toluene disproportionation conditions.

DETAILED DESCRIPTION OF THE PREFERRED EMBODIMENTS

In a first aspect, the invention provides a catalyst for toluene shape selective disproportionation.

The catalyst of the invention comprises 45 to 95 wt %, and preferably 60 to 90 wt % of ZSM-5 molecular sieve. The ZSM-5 molecular sieve in as synthesized form is generally of needle shape. The ZSM-5 molecular sieve used in the invention has an average particle size of from 0.3 to 6 µm, and a molar ratio of $SiO_2/Al_2O_3$ of from 20 to 120, and preferably from 25 to 50.

The catalyst of the invention comprises at least one metal selected from Group IIB metals, Group IIIB metals, rare earth elements and Group VIII metals other than nickel, or oxide(s) thereof, in an amount of from 0.01 to 30 wt %, and preferably from 0.1 to 15 wt %. Preferred Group IIB metals include zinc and cadmium. Preferred Group IIIB metals include scandium and yttrium. Preferred rare earth elements include lanthanum, cerium, praseodymium, neodymium and samarium. Preferred Group VIII metals include iron and cobalt.

The catalyst of the invention comprises at least one metal selected from Group VA metals, Group VIB metals and alkaline earth metals, or oxide(s) thereof, in an amount of from 0 to 20 wt %, and preferably from 0.1 to 10 wt %. Preferred Group VA elements include phosphorus, arsenic, antimony and bismuth. Preferred Group VIB metals include chromium, molybdenum and tungsten.

The catalyst of the invention comprises 1 to 50 wt %, and preferably 2 to 30 wt % of a binder. The binder is preferably at least one selected from $SiO_2$, $Al_2O_3$, $TiO_2$ and clays.

The catalyst of the invention further comprises 1 to 25 wt %, and preferably 1.5 to 20 wt % of a silica inert surface coating derived from an organopolysiloxane. The organopolysiloxane is preferably selected from dimethylpolysiloxane, methylaminopolysiloxane, methylhydroxylpolysiloxane, methylphenylpolysiloxane, methylethylpolysiloxane, methylpropylpolysiloxane, diethylpolysiloxane and mixtures thereof, and more preferably dimethylpolysiloxane. The organopolysiloxane may have a polymerization degree of larger than about 4. In a preferred embodiment, the organopolysiloxane used in the invention has a viscosity of from about 0.02 to 100 Pa·s, preferably from 0.03 to 10 Pa·s, and more preferably from 0.05 to 1 Pa·s at 20° C.

In an embodiment, the catalyst of the invention may be prepared by a process comprising the steps of i) mixing ZSM-5 molecular sieve, a binder precursor, a precursor of all modifying element(s) and water to provide a mixture, and extruding the mixture to provide an extrudate;

ii) drying and optionally calcining the extrudate to give a catalyst precursor;

iii) treating the catalyst precursor with an organopolysiloxane; and iv) calcining the organopolysiloxane-treated catalyst precursor to give the catalyst.

In another embodiment, the catalyst of the invention may be prepared by a process comprising the steps of i) mixing ZSM-5 molecular sieve, a binder precursor, a precursor of part of modifying element(s) and water to provide a mixture, and extruding the mixture to provide an extrudate;

ii) drying and optionally calcining the extrudate;

iii) incorporating the remaining part of the modifying element(s) into the extrudate obtained from step ii) by ion exchange or impregnating process, then drying and optionally calcining the extrudate to give a catalyst precursor;

iv) treating the catalyst precursor with an organopolysiloxane; and v) calcining the organopolysiloxane-treated catalyst precursor to give the catalyst.

In still another embodiment, the catalyst of the invention may be prepared by a process comprising the steps of i) mixing ZSM-5 molecular sieve, a binder precursor and water to provide a mixture, and extruding the mixture to provide an extrudate;

ii) drying and optionally calcining the extrudate;

iii) incorporating all modifying element(s) into the extrudate obtained from step ii) by ion exchange or impregnating process, then drying and optionally calcining the extrudate to give a catalyst precursor;

iv) treating the catalyst precursor with an organopolysiloxane; and v) calcining the organopolysiloxane-treated catalyst precursor to give the catalyst.

The binder precursor may be at least one of $SiO_2$ sol, $Al_2O_3$ sol, $TiO_2$ sol and acid-treated clays (for example, those washed with 1N nitric acid), and it is used in such an amount that will provide a binder content in the final catalyst of from 1 to 50 wt %, and preferably from 2 to 30 wt %.

The precursors of the modifying elements are any compounds that are capable of forming a modifying element oxide upon calcining in air, including, but not limited to, inorganic acids, salts, hydroxides, oxides and organometallic compounds comprising the modifying elements.

In the above processes, the amount of water used may range from 40 to 140 wt %, based on the solid contents of the mixture obtained from step (i). The water may be added separately or as a solvent or a dispersion medium of another component.

The procedures and conditions for the incorporation of the modifying elements into the molecular sieve catalyst by ion exchange or impregnating process per se are known in the art.

The conditions for the drying and the calcining are well known by those skilled in the art. For example, the drying may be performed at a temperature of from about 40 to about 200° C., preferably from about 50 to about 150° C., and more preferably from about 60 to about 100° C. for about 0.5 to about 48 hours, and preferably for about 1 to about 24 hours. The drying may also be conveniently accomplished by drying in air at room temperature. The calcining may be performed at a temperature of from about 250 to about 1100° C., preferably from about 300 to about 900° C., and more preferably from about 350 to about 700° C. for about 1 to about 24 hours, and preferably for about 2 to about 12 hours.

The treatment of the catalyst precursor with an organopolysiloxane may be carried out as follows: the organopolysiloxane compound is dissolved in an inert organic solvent, and the resulting solution is mixed with the catalyst precursor, then the organic solvent is evaporated off. Optionally, when the organic solvent is evaporated, the mixture may be heated and/or applied with a vacuum.

Alternatively, the treatment of the catalyst precursor with an organopolysiloxane may be carried out as follows: the organopolysiloxane compound is dissolved in an inert organic solvent, and the resulting solution is sprayed on heated catalyst precursor in a drum dryer, thereby forming an organopolysiloxane coating on the catalyst precursor.

Examples of the inert organic solvent include, but are not limited to, n-pentane, n-hexane, n-heptane and cyclohexane. The concentration of the organopolysiloxane compound in the solution in the organic solvent is not specifically limited, but, in general, it conveniently ranges from 5 to 40 wt %, and preferably from 10 to 30 wt %. The treatment may be carried out for one or more times. The organopolysiloxane is used in such an amount that will provide a silica coating content in the final catalyst of from 1 to 25 wt %, and preferably from 1.5 to 20 wt %.

In a second aspect, the present invention provides a process for shape selectively disproportionating toluene into p-xylene, comprising contacting a reaction stream containing toluene with the catalyst for toluene shape selective disproportionation according to the invention under toluene disproportionation conditions.

The present invention may use those toluene disproportionation processes and conditions known by those skilled in the art. The process may be carried out in a batch reactor, or in a fluidized or fixed bed reactor.

In a preferred embodiment, the process is carried out in a fixed bed reactor, and may employ the following reaction conditions: a temperature at reactor inlet of from about 350 to about 540° C., and preferably from about 400 to about 500° C.; a pressure of from about 0.1 to about 30 MPa, and preferably from about 0.5 to about 7 MPa; a WHSV of from about 0.1 to 20 $h^{-1}$, and preferably from 1.0 to 5.0 $h^{-1}$; and a molar ratio of hydrogen to hydrocarbons of from about 0.1 to 20, and preferably from about 1 to 5.

The catalyst of the invention has a higher catalytic activity for the toluene selective disproportionation and a higher p-xylene selectivity, and will not cause remarkable toluene hydrogenation and dealkylation side-reactions.

EXAMPLES

The following examples are given for further illustrating the invention.

Example 1

36 g of ZSM-5 in hydrogen form having an average particle size of 1.7 μm and a molar ratio of $SiO_2/Al_2O_3$ of 31 was kneaded with 33.2 g of a silica sol (containing 12 wt % of $SiO_2$), 0.8 g of chemically pure zinc nitrate [$Zn(NO_3)_2 \cdot 6H_2O$] and 2 ml of water, and then extruded to form cylindrical extrudates having a diameter of 1.7 mm. The extrudates were dried in air, and then calcined in air at 520° C. for 2 hours, to give a shaped catalyst precursor.

The above catalyst precursor was added to a solution formed from 40 ml of n-hexane and 10.0 g of dimethylpolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool. The above modifying procedure was repeated, to give a twice shape selectivated catalyst A with a gain of the catalyst mass of 22%.

Example 2

32 g of ZSM-5 in hydrogen form having an average particle size of 2.2 μm and a molar ratio of $SiO_2/Al_2O_3$ of 50 was kneaded with 24 g of a titania sol (containing 25 wt % of $TiO_2$), 3.72 g of chemically pure scandium nitrate [$Sc(NO_3)_3 \cdot 5H_2O$], 0.2 ml of chemically pure nitric acid and 8 ml of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 8.0 g of methylaminopolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool. The above modifying procedure was then repeated, to give a twice shape selectivated catalyst B with a gain of the catalyst mass of 18%.

Example 3

28 g of ZSM-5 in hydrogen form having an average particle size of 4 μm and a molar ratio of $SiO_2/Al_2O_3$ of 60 was kneaded with 22.4 g of a titania sol (containing 27 wt % of $TiO_2$), 4.6 g of acid-treated clay (obtained by soaking 1 part by weight of clay in 3 parts by weight of 1N aqueous solution of nitric acid at ambient temperature for 6 hours, then filtering the clay and washing it with water to near neutrality, and then calcining the resulting solids at 550° C. for 4 hours), 0.11 g of chemically pure cerium nitrate [$Ce(NO_3)_3 \cdot 6H_2O$], 7.36 g of chemically pure chromium nitrate [$Cr(NO_3)_3 \cdot 9H_2O$], 0.2 ml of chemically pure nitric acid and 5 ml of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 4 g of methylaminopolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool. The above modifying procedure was repeated, to give a twice shape selectivated catalyst C with a gain of the catalyst mass of 8%.

Example 4

24 g of ZSM-5 in hydrogen form having an average particle size of 3 μm and a molar ratio of $SiO_2/Al_2O_3$ of 25 was kneaded with 10 g of a silica sol (containing 40 wt % of $SiO_2$), 6.0 g of acid-treated clay (obtained by soaking 1 part by weight of clay in 3 parts by weight of 1N aqueous solution of nitric acid at ambient temperature for 6 hours, then filtering the clay and washing it with water to near neutrality, and then calcining the resulting solids at 550° C. for 4 hours), 14.14 g of chemically pure ferric nitrate [$Fe(NO_3)_3 \cdot 9H_2O$], 4.28 g of chemically pure ammonium molybdate [$(NH_4)_6Mo_7O_{24} \cdot 6H_2O$], 0.2 ml of chemically pure nitric acid and 26 ml of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 2.4 g of dimethylpolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool. The above modifying procedure was repeated, to give a twice shape selectivated catalyst D with a gain of the catalyst mass of 5%.

Example 5

19.2 g of ZSM-5 in hydrogen form having an average particle size of 3 μm and a molar ratio of $SiO_2/Al_2O_3$ of 112 was kneaded with 6.8 g of acid-treated clay (obtained by soaking 1 part by weight of clay in 3 parts by weight of 1N aqueous solution of nitric acid at ambient temperature for 6 hours, then filtering the clay and washing it with water to near neutrality, and then calcining the resulting solids at 550° C. for 4 hours), 11.55 g of chemically pure cadmium nitrate [$Cd(NO_3)_2 \cdot 4H_2O$], 8.43 g of chemically pure praseodymium nitrate [Pr(NO$_3$)$_3$.6H$_2$O], 29.48 g of chemically pure chromium nitrate [Cr(NO$_3$)$_3$.9H$_2$O], 1.68 g of chemically pure calcium nitrate [Ca(NO$_3$)$_2$.4H$_2$O], 0.2 ml of chemically pure nitric acid and 24 ml of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 1.2 g of methylhydroxylpolysiloxane having a viscosity of 0.08 Pa·s at 20° C., and then the n-hexane was distilled off in an oil bath at 90° C. After the distilling, the residues were calcined in a muffle furnace at 520° C. for 3 hours and then allowed to cool. The above modifying procedure was repeated, to give a twice shape selectivated catalyst E with a gain of the catalyst mass of 2%.

Example 6

26 g of ZSM-5 in hydrogen form having an average particle size of 1.8 μm and a molar ratio of SiO$_2$/Al$_2$O$_3$ of 100 was kneaded with 15 g of a silica sol (containing 40 wt % of SiO$_2$), 11.70 g of chemically pure zinc nitrate [Zn(NO$_3$)$_2$.6H$_2$O], 10.88 g of chemically pure cobalt nitrate [CoNO$_3$]$_2$.6H$_2$O], 1.60 g of chemically pure ammonium molybdate [(NH$_4$)$_6$Mo$_7$O$_{24}$.6H$_2$O], 0.68 g of chemically pure barium nitrate [Ba(NO$_3$)$_2$], 0.46 g of chemically pure phosphoric acid and 26 ml of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 8 g of methylaminopolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool, to give a once shape selectivated catalyst precursor.

The above once shape selectivated catalyst precursor was added to a solution formed from 40 ml of n-hexane and 14 g of methylphenylpolysiloxane having a viscosity of 0.2 Pa·s at 20° C., and then the n-hexane was distilled off in an oil bath at 90° C. After the distilling, the residues were calcined in a muffle furnace at 520° C. for 3 hours and then allowed to cool, to give a twice shape selectivated catalyst F with a gain of the catalyst mass of 15%.

Example 7

22 g of ZSM-5 in hydrogen form having an average particle size of 5 μm and a molar ratio of SiO$_2$/Al$_2$O$_3$ of 90 was kneaded with 8 g of a silica sol (containing 20 wt % of SiO$_2$), 0.46 g of chemically pure palladium nitrate [Pb(NO$_3$)$_2$.H$_2$O], 19.57 g of chemically pure niobium nitrate [Nb(NO$_3$)$_3$.XH$_2$O], 8.76 g of chemically pure zinc nitrate [Zn(NO$_3$)$_2$.6H$_2$O], 12.85 g of chemically pure antimony acetate [Sb(CH$_3$COO)$_3$], 5.08 g of chemically pure magnesium nitrate [Mg(NO$_3$)$_2$.6H$_2$O], 0.5 ml of chemically pure nitric acid and 26 ml of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 2 g of methylphenylpolysiloxane having a viscosity of 0.2 Pa·s at 20° C., and then the n-hexane was distilled off in an oil bath at 90° C. After the distilling, the residues were calcined in a muffle furnace at 520° C. for 3 hours and then allowed to cool. The above modifying procedure was repeated, to give a twice shape selectivated catalyst G with a gain of the catalyst mass of 2%.

Example 8

30 g of ZSM-5 in hydrogen form having an average particle size of 4.5 μm and a molar ratio of SiO$_2$/Al$_2$O$_3$ of 42 was kneaded with 30 g of a silica sol (containing 20 wt % of SiO$_2$), 13.16 g of chemically pure zinc nitrate [Zn(NO$_3$)$_2$.6H$_2$O] and 1.06 g of chemically pure cerium nitrate [Ce(NO$_3$)$_3$.6H$_2$O], and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 10 g of dimethylpolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool. The above modifying procedure was repeated, to give a twice shape selectivated catalyst H with a gain of the catalyst mass of 20%.

Example 9

24 g of ZSM-5 in hydrogen form having an average particle size of 2.5 μm and a molar ratio of SiO$_2$/Al$_2$O$_3$ of 34 was kneaded with 5.6 g of acid-treated clay (obtained by soaking 1 part by weight of clay in 3 parts by weight of 1N aqueous solution of nitric acid at ambient temperature for 6 hours, then filtering the clay and washing it with water to near neutrality, and then calcining the resulting solids at 550° C. for 4 hours), 20.17 g of chemically pure lanthanum acetate [La(CH$_3$COO)$_3$], 0.01 g of chemically pure ammonium para-tungstate [(NH$_4$)$_{10}$H$_2$(W$_2$O$_7$)$_6$.H$_2$O], 0.02 g of chemically pure bismuth nitrate [Bi(NO$_3$)$_3$.6H$_2$O], 0.4 ml of nitric acid and 24 g of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 0.8 g of dimethylpolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool, to give a once shape selectivated catalyst precursor.

The above once shape selectivated catalyst precursor was added to a solution formed from 40 ml of n-hexane and 0.8 g of methylaminopolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool, to give a twice shape selectivated catalyst precursor.

The above twice shape selectivated catalyst precursor was added to a solution formed from 40 ml of n-hexane and 0.8 g of methylhydroxylpolysiloxane having a viscosity of 0.08 Pa·s at 20° C., and then the n-hexane was distilled off in an oil bath at 90° C. After the distilling, the residues were calcined in a muffle furnace at 520° C. for 3 hours and then allowed to cool, to give a thrice shape selectivated catalyst I with a gain of the catalyst mass of 3%.

Example 10

28 g of ZSM-5 in hydrogen form having an average particle size of 2.8 μm and a molar ratio of SiO$_2$/Al$_2$O$_3$ of 34 was kneaded with 14 g of a silica sol (containing 20 wt % of SiO$_2$), 16.19 g of chemically pure ferric nitrate [Fe(NO$_3$)$_3$.9H$_2$O], 4.23 g of chemically pure cerium nitrate [Ce(NO$_3$)$_3$.6H$_2$O], 1.02 g of chemically pure samarium nitrate [Sm(NO$_3$)$_3$.6H$_2$O], 7.77 g of chemically pure bismuth nitrate [Bi(NO$_3$)$_3$.6H$_2$O], 1.27 g of chemically pure magnesium nitrate [Mg(NO$_3$)$_2$.6H$_2$O], 1.06 g of chemically pure chromium nitrate [Cr(NO$_3$)$_3$9H$_2$O], 0.4 ml of nitric acid and 24 g of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 6 g of dimethylpolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool. The above modifying procedure was repeated, to give a twice shape selectivated catalyst J with a gain of the catalyst mass of 12%.

Comparative Example 1

24 g of ZSM-5 in hydrogen form having an average particle size of 3 μm and a molar ratio of SiO$_2$/Al$_2$O$_3$ of 25 was kneaded with 20 g of a silica sol (containing 40 wt % of SiO$_2$), 7.6 g of acid-treated clay (obtained by soaking 1 part by weight of clay in 3 parts by weight of 1N aqueous solution of nitric acid at ambient temperature for 6 hours, then filtering the clay and washing it with water to near neutrality, and then calcining the resulting solids at 550° C. for 4 hours), 0.66 g of chemically pure palladium nitrate [Pb(NO$_3$)$_3$.H$_2$O], 0.2 ml of chemically pure nitric acid and 10 ml of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 1.2 g of dimethylpolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool. The above modifying procedure was repeated, to give a twice shape selectivated comparative catalyst 1 with a gain of the catalyst mass of 2%.

Comparative Example 2

36 g of ZSM-5 in hydrogen form having an average particle size of 11 μm and a molar ratio of SiO$_2$/Al$_2$O$_3$ of 31 was kneaded with 26.5 g of a silica sol (containing 40 wt % of SiO$_2$), 0.0.8 g of chemically pure zinc nitrate [Zn(NO$_3$)$_2$.6H$_2$O], 0.04 g of chemically pure 85% phosphoric acid, 0.02 g of chemically pure ammonium molybdate [(NH$_4$)$_6$Mo$_7$O$_{24}$.6H$_2$O] and 8 ml of water, and then extruded to form cylindrical extrudates having a diameter of 1.7 mm. The extrudates were dried in air, and then calcined at 520° C. for 2 hours, to give a shaped catalyst precursor.

The above catalyst precursor was added to a solution formed from 40 ml of n-hexane and 8 g of dimethylpolysiloxane having a viscosity of 0.1 Pa·s at 20° C., and then the n-hexane was distilled off in an oil bath at 90° C. After the distilling, the residues were calcined in a muffle furnace at 520° C. for 3 hours and then allowed to cool. The above modifying procedure was repeated, to give a twice shape selectivated comparative catalyst 2 with a gain of the catalyst mass of 18%.

Example 13

The catalysts A to J as prepared in Examples 1 to 10 were evaluated on a fixed bed evaluation equipment to obtain their catalytic activities for toluene disproportionation and selectivities. The amount of the catalysts loaded was 5.0 g, weight hourly space velocity was 4.0 h$^{-1}$, reaction temperature was 425° C., reaction pressure was 2.1 MPa, and the molar ratio of hydrogen to hydrocarbons was 2. The reaction results are shown in the Table 1 below. The evaluation results of the comparative catalysts 1 and 2 obtained under the same conditions are presented for comparison.

Toluene conversion=(the weight of toluene fed to the reactor–the weight of toluene exiting the reactor)/(the weight of toluene fed to the reactor)×100% p-Selectivity=(the content of p-xylene in the reaction effluent)/(the content of xylenes in the reaction effluent)×100%

TABLE 1

Results of catalyst evaluation

| Catalyst | Molar ratio of benzene to p-xylene | Toluene conversion % | p-Xylene selectivity % |
|---|---|---|---|
| A | 1.53 | 30.1 | 93.2 |
| B | 1.30 | 27.8 | 93.5 |
| C | 1.45 | 26.0 | 92.0 |
| D | 1.28 | 31.5 | 94.5 |
| E | 1.15 | 15.0 | 95.4 |
| F | 1.43 | 19.3 | 96.2 |
| G | 1.50 | 20.2 | 96.0 |
| H | 1.32 | 28.5 | 90.1 |
| I | 1.25 | 30.2 | 94.5 |
| J | 1.35 | 31.6 | 95.3 |
| Comp. Catalyst 1 | 1.53 | 29.5 | 89.3 |
| Comp. Catalyst 2 | 1.60 | 27.1 | 92.0 |

The Table 2 below summarizes the Examples 1-10 and the Comparative Examples 1-2.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

TABLE 2

The summary of the Examples 1-10 and the Comparative Examples 1-2

| | a) ZSM-5 | | | b) | | c) | | d) Silica coating | | e) Binder | |
|---|---|---|---|---|---|---|---|---|---|---|---|
| | Content* wt % | Average Particle size μm | SiO$_2$/Al$_2$O$_3$ | Content* wt % | Metal | Content* wt % | Metal | Content** wt % | Source | Content* wt % | Source |
| Ex. 1 | 90 | 1.7 | 31 | 0.05 | Zn | 0.1 | W P | 22 | Dimethylpolysiloxane | The Balance | SiO$_2$ sol |
| Ex. 2 | 80 | 2.2 | 50 | 2 | Sc | 0 | / | 18 | Methylaminopolysiloxane | The Balance | TiO$_2$ sol |

TABLE 2-continued

The summary of the Examples 1-10 and the Comparative Examples 1-2

| | a) ZSM-5 | | | b) | | c) | | d) Silica coating | | e) Binder | |
|---|---|---|---|---|---|---|---|---|---|---|---|
| | Content* wt % | Average Particle size μm | SiO$_2$/ Al$_2$O$_3$ | Content* wt % | Metal | Content* wt % | Metal | Content** wt % | Source | Content* wt % | Source |
| Ex. 3 | 70 | 4 | 60 | 0.1 | Ce | 3.5 | Cr | 8 | Methylaminopolysiloxane | The Balance | TiO$_2$ sol |
| Ex. 4 | 60 | 3 | 25 | 7 | Fe | 8 | Mo | | Dimethylpolysiloxane | The Balance | SiO$_2$ sol |
| Ex. 5 | 48 | 3 | 112 | 20 | Cd Pr | 15 | Cr Ca | 5 | Methylhydroxylpolysiloxane | The Balance | Acid-treated clay |
| Ex. 6 | 65 | 1.8 | 100 | 15 | Zn Co | 5 | P Mo Ba | 2 | Methylaminopolysiloxane, Methylphenylpolysiloxane | The Balance | SiO$_2$ sol |
| Ex. 7 | 55 | 5 | 90 | 23 | Pd Nd Zn | 18 | Sb Mg | 8 | Methylphenylpolysiloxane | The Balance | SiO$_2$ sol |
| Ex. 8 | 75 | 4.5 | 42 | 10 | Zn Ce | 0 | / | 4 | Dimethylpolysiloxane | The Balance | TiO$_2$ sol |
| Ex. 9 | 60 | 2.5 | 34 | 26 | La | 0.05 | W Bi | 20 | Dimethylpolysiloxane, Methylaminopolysiloxane, Methylhydroxylpolysiloxane | The Balance | Acid-treated clay |
| Ex. 10 | 70 | 2.8 | 34 | 13 | Fe Ce Sm | 10 | Bi Mg Cr | 3 | Dimethylpolysiloxane | The Balance | SiO$_2$ sol |
| Comp. Ex. 1 | 60 | 3 | 25 | 7 | Pd | / | / | 12 | Dimethylpolysiloxane | The Balance | SiO$_2$ sol |
| Comp. Ex. 2 | 90 | 11 | 31 | 0.05 | Zn | 0.1 | Mo P | 18 | Dimethylpolysiloxane | The Balance | SiO$_2$ sol |

*Calculated by taking the weight of the catalyst precursor before the shape selectivating treatment as 100%.
**Meaning the weight gain of the catalyst precursor after the shape selectivating treatment.

What is claimed is:

1. A catalyst for toluene shape selective disproportionation, consisting essentially of:
   a) 45 to 95 wt % of ZSM-5 molecular sieve having an average particle size of from 0.3 to 6 μm and a molar ratio of SiO$_2$ to Al$_2$O$_3$ of from 20 to 120;
   b) 0.1 to 30 wt % of at least one metal selected from the group consisting of Group IIB metals, Group IIIB metals, rare earth elements, iron and cobalt or oxide(s) thereof;
   c) 0 to 20 wt % of at least one metal selected from the group consisting of Group VA metals, Group VIB metals and alkaline earth metals, or oxide(s) thereof;
   d) 1 to 25 wt % of a silica inert surface coating derived from an organopolysiloxane; and
   e) 1 to 50 wt % of a binder.

2. The catalyst of claim 1, wherein the binder is at least one selected from the group consisting of SiO$_2$, Al$_2$O$_3$, TiO$_2$ and clays.

3. The catalyst of claim 1, wherein the ZSM-5 molecular sieve has a molar ratio of SiO$_2$/Al$_2$O$_3$ of from 25 to 50.

4. The catalyst of claim 1, wherein the content of the ZSM-5 molecular sieve ranges from 60 to 95 wt %.

5. The catalyst of claim 1, wherein the content of the at least one metal selected from the group consisting of Group IIB metals, Group IIIB metals, rare earth elements iron and cobalt or oxide(s) thereof, ranges from 0.1 to 15 wt %.

6. The catalyst of claim 1, wherein the content of the at least one metal selected from the group consisting of Group VA metals, Group VIB metals and alkaline earth metals, or oxide(s) thereof; ranges from 0.1 to 10 wt %.

7. The catalyst of claim 1, wherein the Group IIB element is at least one of zinc and cadmium, the Group IIIB metal is at least one of scandium and yttrium, the rare earth element is at least one of lanthanum, cerium, praseodymium, neodymium and samarium, the Group VA element is at least one of phosphorus, arsenic, antimony and bismuth, and the Group VIB element is at least one of chromium, molybdenum and tungsten.

8. The catalyst of claim 1, wherein the organopolysiloxane is selected from the group consisting of dimethylpolysiloxane, methylaminopolysiloxane, methylhydroxylpolysiloxane, methylphenylpolysiloxane, methylethylpolysiloxane, methylpropylpolysiloxane, diethylpolysiloxane and mixtures thereof.

9. The catalyst of claim 8, wherein the organopolysiloxane is dimethylpolysiloxane.

10. A process for preparing the catalyst for toluene shape selective disproportionation according to claim 1, which process comprises the steps of
   i) mixing ZSM-5 molecular sieve having an average particle size of from 0.3 to 6 μm and a molar ratio of SiO$_2$ to Al$_2$O$_3$ of from 20 to 120, a binder precursor, a precursor of modifying element(s) comprising at least one metal selected from the group consisting of Group II B metal, Group III B metal, rare earth elements, iron and cobalt, and optionally at least one metal selected from the group consisting of Group VA metals, Group VI B metals and alkaline earth metals or oxide(s) thereof, and water to provide a mixture, and extruding the mixture to provide an extrudate;
   ii) drying and optionally calcining the extrudate to give a catalyst precursor;
   iii) treating the catalyst precursor with an organopolysiloxane; and
   iv) calcining the organopolysiloxane-treated catalyst precursor to give the catalyst.

11. The process of claim 10, wherein the binder precursor is at least one of SiO$_2$ sol, Al$_2$O$_3$ sol, TiO$_2$ sol and acid-treated clays, and it is used in such an amount that will provide a binder content in the final catalyst of from 1 to 50 wt %.

12. The process of claim 10, wherein the amount of water used ranges from 40 to 140 wt %, based on the solid contents of the mixture obtained from step (i), and wherein the water is added separately or as a solvent or a dispersion medium of another component.

13. The process of claim 10, wherein the treatment of the catalyst precursor with an organopolysiloxane is carried out as follows:

the organopolysiloxane compound is dissolved in an inert organic solvent, and the resulting solution is mixed with the catalyst precursor, then the organic solvent is evaporated off while optionally heating the mixture and/or applying a vacuum thereon;

alternatively, the organopolysiloxane compound is dissolved in an inert organic solvent, and the resulting solution is sprayed on heated catalyst precursor in a drum dryer, thereby forming an organopolysiloxane coating on the catalyst precursor.

14. A process for shape selectively disproportionating toluene into p-xylene, comprising contacting a reaction stream containing toluene with the catalyst for toluene shape selective disproportionation according to claim 1 under toluene disproportionation conditions.

15. A catalyst for toluene shape selective disproportionation, consisting of:
    a) 45 to 95 wt % of ZSM-5 molecular sieve having an average particle size of from 0.3 to 6 μm and a molar ratio of $SiO_2$ to $Al_2O_3$ of from 20 to 120;
    b) 0.1 to 30 wt % of at least one metal selected from the group consisting of Group IIB metals, Group IIIB metals, rare earth elements, iron and cobalt Group VIII metals other than nickel, or oxide(s) thereof;
    c) 0 to 20 wt % of at least one metal selected from the group consisting of Group VA metals, Group VIB metals and alkaline earth metals, or oxide(s) thereof;
    d) 1 to 25 wt % of a silica inert surface coating derived from an organopolysiloxane; and
    e) 1 to 50 wt % of a binder.

16. A process for preparing the catalyst for toluene shape selective disproportionation according to claim 1, which process comprises the steps of
    i) mixing ZSM-5 molecular sieve having an average particle size of from 0.3 to 6 μm and a molar ratio of $SiO_2$ to $Al_2O_3$ of from 20 to 120; a binder precursor; a portion of a precursor of modifying element(s), said modifying element(s) comprising at least one metal selected from the group consisting of Group IIB metals, Group IIIB metals, rare earth elements, iron and cobalt or oxide(s) thereof; and optionally at least one metal selected from the group consisting of Group VA metals, Group VIB metals and alkaline earth metals, or oxide(s) thereof; and water to provide a mixture, and extruding the mixture to provide an extrudate;
    ii) drying and optionally calcining the extrudate;
    iii) incorporating the remaining portion of the precursor of the modifying element(s) into the extrudate obtained from step ii) by ion exchange or impregnating process, then drying and optionally calcining the extrudate to give a catalyst precursor;
    iv) treating the catalyst precursor with an organopolysiloxane; and
    v) calcining the organopolysiloxane-treated catalyst precursor to give the catalyst.

17. A process for preparing the catalyst for toluene shape selective disproportionation according to claim 1, which process comprises the steps of
    i) mixing ZSM-5 molecular sieve having an average particle size of from 0.3 to 6 μm and a molar ratio of $SiO_2$ to $Al_2O_3$ of from 20 to 120; a binder precursor; and water to provide a mixture, and extruding the mixture to provide an extrudate;
    ii) drying and optionally calcining the extrudate;
    iii) incorporating modifying element(s) into the extrudate obtained from step ii) by ion exchange or impregnating process, then drying and optionally calcining the extrudate to give a catalyst precursor, said modifying element(s) comprising at least one metal selected from the group consisting of Group IIB metals, Group IIIB metals, rare earth elements, iron and cobalt or oxide(s) thereof; and optionally at least one metal selected from the group consisting of Group VA metals, Group VIB metals and alkaline earth metals, or oxide(s) thereof;
    iv) treating the catalyst precursor with an organopolysiloxane; and
    v) calcining the organopolysiloxane-treated catalyst precursor to give the catalyst.

18. The process of claim 16, wherein the binder precursor is at least one of $SiO_2$ sol, $Al_2O_3$ sol, $TiO_2$ sol and acid-treated clays, and it is used in such an amount that will provide a binder content in the final catalyst of from 1 to 50 wt %.

19. The process of claim 17, wherein the binder precursor is at least one of $SiO_2$ sol, $Al_2O_3$ sol, $TiO_2$ sol and acid-treated clays, and it is used in such an amount that will provide a binder content in the final catalyst of from 1 to 50 wt %.

20. The process of claim 16, wherein the amount of water used ranges from 40 to 140 wt %, based on the solid contents of the mixture obtained from step (i), and wherein the water is added separately or as a solvent or a dispersion medium of another component.

21. The process of claim 17, wherein the amount of water used ranges from 40 to 140 wt %, based on the solid contents of the mixture obtained from step (i), and wherein the water is added separately or as a solvent or a dispersion medium of another component.

22. The process of claim 16, wherein the treatment of the catalyst precursor with an organopolysiloxane is carried out as follows:

the organopolysiloxane compound is dissolved in an inert organic solvent, and the resulting solution is mixed with the catalyst precursor, then the organic solvent is evaporated off while optionally heating the mixture and/or applying a vacuum thereon;

alternatively, the organopolysiloxane compound is dissolved in an inert organic solvent, and the resulting solution is sprayed on heated catalyst precursor in a drum dryer, thereby forming an organopolysiloxane coating on the catalyst precursor.

23. The process of claim 17, wherein the treatment of the catalyst precursor with an organopolysiloxane is carried out as follows:

the organopolysiloxane compound is dissolved in an inert organic solvent, and the resulting solution is mixed with the catalyst precursor, then the organic solvent is evaporated off while optionally heating the mixture and/or applying a vacuum thereon;

alternatively, the organopolysiloxane compound is dissolved in an inert organic solvent, and the resulting solution is sprayed on heated catalyst precursor in a drum dryer, thereby forming an organopolysiloxane coating on the catalyst precursor.

* * * * *